US010545101B2

(12) United States Patent
Sugita et al.

(10) Patent No.: US 10,545,101 B2
(45) Date of Patent: Jan. 28, 2020

(54) INSPECTION APPARATUS

(71) Applicant: OMRON Corporation, Kyoto-shi, Kyoto (JP)

(72) Inventors: Shinji Sugita, Kyoto (JP); Takako Onishi, Kyotanabe (JP); Yoshihide Ota, Kusatsu (JP)

(73) Assignee: OMRON Corporation, Kyoto-shi (JP)

( * ) Notice: Subject to any disclaimer, the term of this patent is extended or adjusted under 35 U.S.C. 154(b) by 167 days.

(21) Appl. No.: 15/603,583

(22) Filed: May 24, 2017

(65) Prior Publication Data

US 2017/0356860 A1    Dec. 14, 2017

(30) Foreign Application Priority Data

Jun. 10, 2016    (JP) .................................. 2016-116148

(51) Int. Cl.
*G01N 23/04*    (2018.01)
*G01N 23/046*    (2018.01)
(Continued)

(52) U.S. Cl.
CPC ........... *G01N 23/046* (2013.01); *B65G 15/00* (2013.01); *G01N 23/04* (2013.01); *G01N 23/18* (2013.01);
(Continued)

(58) Field of Classification Search
None
See application file for complete search history.

(56) References Cited

U.S. PATENT DOCUMENTS 3,678,278 A * 7/1972 Peil ...................... G01V 5/0008
250/515.1
4,210,811 A * 7/1980 Dennhoven ............ G01N 23/04
250/358.1
(Continued)

FOREIGN PATENT DOCUMENTS

CN      101393142 A    3/2009
JP      2000-012999 A  1/2000
(Continued)

OTHER PUBLICATIONS

The Chinese Office Action (CNOA) dated Aug. 2, 2019 in a counterpart Chinese patent application.

*Primary Examiner* — Hoon K Song
(74) *Attorney, Agent, or Firm* — Metrolex IP Law Group, PLLC

(57) ABSTRACT

An inspection apparatus includes a feed-in preparation chamber, an imaging chamber, and a feed-out preparation chamber. Each preparation chamber includes a feed-in unit that receives an inspection object through a first opening, a traverser that translates the received object to a second opening in a direction different from the receiving direction of the object, and a feed-out unit that moves the object in a direction different from a moving direction of the traverser and discharges the object through the second opening. The imaging chamber includes an imaging unit that images the object fed from the feed-in preparation chamber. The traverser includes a mount for the object, and a shield that moves together with the mount and prevents radioactive rays entering one of the first and second openings and propagating in the moving direction of the traverser from reaching the other opening.

11 Claims, 9 Drawing Sheets

(51) Int. Cl.
*B65G 15/00* (2006.01)
*G01N 23/18* (2018.01)
*G01V 5/00* (2006.01)
*G21K 1/04* (2006.01)

(52) U.S. Cl.
CPC ............ *G01V 5/0016* (2013.01); *G21K 1/04* (2013.01); *G01N 2223/3307* (2013.01); *G01N 2223/3308* (2013.01); *G01N 2223/419* (2013.01); *G01N 2223/643* (2013.01); *G01N 2223/646* (2013.01)

(56) References Cited

U.S. PATENT DOCUMENTS

| | | | | |
|---|---|---|---|---|
| 5,491,737 | A | * | 2/1996 | Yarnall .................. G01N 23/04 378/58 |
| 8,513,623 | B2 | * | 8/2013 | Newman .................. A61L 2/081 250/455.11 |
| 2010/0329532 | A1 | | 12/2010 | Masuda et al. |
| 2014/0064440 | A1 | * | 3/2014 | Hara ....................... A61B 6/508 378/4 |
| 2016/0372223 | A1 | * | 12/2016 | Splinter ................. G01N 23/04 |

FOREIGN PATENT DOCUMENTS

| | | |
|---|---|---|
| JP | 2009-156788 A | 7/2009 |
| JP | 2014-098567 A | 5/2014 |

\* cited by examiner

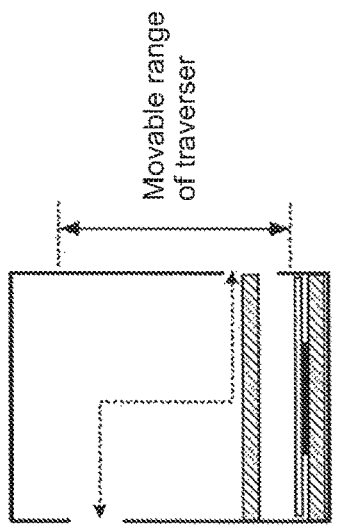
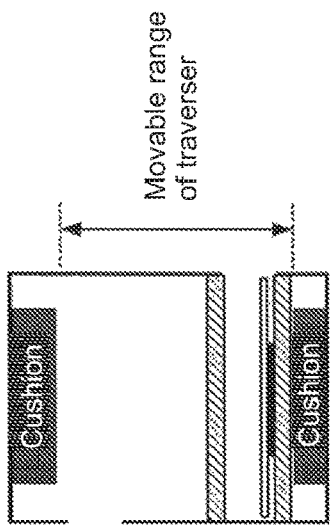
Fig. 9A
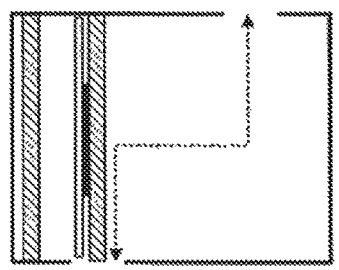
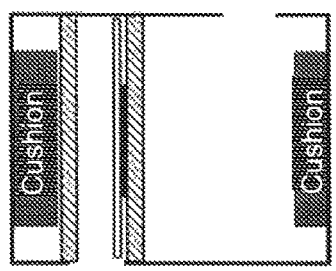
Fig. 9B
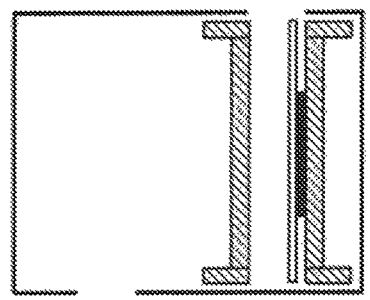
Fig. 10

INSPECTION APPARATUS

CROSS REFERENCE TO RELATED APPLICATIONS

This application claims priority from prior Japanese Patent Application No. 2016-116148 filed with the Japan Patent Office on Jun. 10, 2016, the entire contents of which are incorporated herein by reference.

FIELD

The present disclosure relates to an inspection apparatus that uses radioactive rays.

BACKGROUND

Inspection techniques known in the art may use image information obtained from X-ray imaging of an inspection object to perform non-destructive inspection of the object. For example, Patent Literature 1 describes a technique for reconstructing three-dimensional (3D) data representing components mounted on a substrate with X-ray computed tomography (CT), and determining whether, for example, the solder is defective or non-defective based on the 3D data. This type of X-ray inspection apparatus, which can inspect the internal structure or the microstructure of the object with high accuracy, is now used in, for example, automatic inspection performed in production lines of various industrial products.

In-line inspection apparatuses may minimize the cycle time for inspection to prevent delays in the inspection process. A known structure as described in Patent Literature 2 uses two feeding lines arranged in parallel (referred to as dual lanes), on one of which an inspection object is inspected, and on the other one of which a subsequent inspection object is fed to the inspection position at the same time. This structure achieves substantially close-to-zero time taken for feeding the object to the inspection position.

However, an X-ray inspection apparatus having this structure receives a subsequent inspection object fed into the apparatus during irradiation of X-rays. The X-ray inspection apparatus may thus have the structure for preventing X-rays from leaking outside the apparatus.

An inspection apparatus described in Patent Literature 3 includes two shutters for each of a feed-in unit and a feed-out unit to prevent an imaging unit from being exposed outside when an inspection object is fed in and fed out. This apparatus allows smooth reception and discharge of an inspection object while preventing leakage of X-rays.

CITATION LIST

Patent Literature

Patent Literature 1: Japanese Unexamined Patent Application Publication No. 2009-156788
Patent Literature 2: Japanese Unexamined Patent Application Publication No. 2000-12999
Patent Literature 3: Japanese Unexamined Patent Application Publication No. 2014-098567

SUMMARY

Technical Problem

However, the use of a plurality of shield shutters as in the inspection apparatus described in Patent Literature 3 complicates the structure of the shutters and their control, and increases the cost of the apparatus. Also, the dual lane structure combined with the technique described in Patent Literature 3 can increase the size of the shutters, and lower the inspection speed.

In response to this issue, one or more aspects of the present invention are directed to a technique for shortening the inspection time and preventing leakage of radioactive rays in an inspection apparatus that uses radioactive rays.

Solution to Problem

The inspection apparatus according to a first embodiment of the present invention includes three compartments, namely, a feed-in preparation chamber, an imaging chamber, and a feed-out preparation chamber.

In detail, each of the feed-in preparation chamber and the feed-out preparation chamber includes a feed-in unit that receives an inspection object through a first opening, a traverser that translates the received inspection object to a second opening in a direction different from a direction in which the inspection object is received, and a feed-out unit that moves the inspection object in a direction different from a moving direction of the traverser, and discharges the inspection object through the second opening. The imaging chamber includes an imaging unit that images the inspection object that is received from the feed-in preparation chamber. The traverser includes a mount on which the inspection object is mountable, and a shield that moves together with the mount, and prevents radioactive rays that enter through one of the first opening and the second opening and propagate in the moving direction of the traverser from reaching the other one of the first opening and the second opening.

The imaging chamber allows imaging of an inspection object using radioactive rays, such as X-rays. The feed-in preparation chamber allows an inspection object to wait until the object is fed into the imaging chamber. The feed-out preparation chamber allows the inspection object that has undergone imaging to be discharged.

An inspection apparatus that performs imaging using radioactive rays may have leakage of radioactive rays when an inspection object is fed into and out of the imaging chamber. The inspection apparatus according to the aspect of the present invention includes the feed-in preparation chamber and the feed-out preparation chamber to keep radioactive rays inside.

Each of the feed-in preparation chamber and the feed-out preparation chamber receives the inspection object through its first opening, moves the object using the traverser, and then discharges the inspection object through its second opening. In other words, the feed-in preparation chamber has its first opening communicating with the outside, and its second opening communicating with the imaging chamber. The feed-out preparation chamber has its first opening communicating with the imaging chamber, and its second opening communicating with the outside.

The traverser translates the inspection object in a direction different from the direction in which the inspection object is received and discharged through the openings. The traverser includes a shield, which is arranged to prevent radioactive rays that enter through one opening from reaching the other opening. The shield is positioned to prevent the first opening and the second opening from communicating with each other when the traverser is at any position, and moves together with the mount.

This structure eliminates a special mechanism, such as a shutter, and allows the inspection object to be fed into and out while preventing the imaging chamber from communicating with the outside.

The shield may include a first member and a second member. The first member and the second member may be positioned to define a closed space together with opposing inner walls of the feed-in preparation chamber or the feed-out preparation chamber while the traverser is moving.

The shields are positioned to define the closed space together with the opposing inner walls. The compartment is thus independent and is like an airlock on the path for feeding the inspection object into and out of the compartment. In other words, this structure allows an inspection object to be fed in and out while preventing the first opening and the second opening from communicating with each other.

In the inspection apparatus according to the above aspect of the present invention, the first opening and the second opening may be spatially separated by the closed space.

Spatially separating the first opening and the second opening prevents radioactive rays from leaking outside the apparatus.

The first member and the second member may be plates that are arranged in parallel with the mount sandwiched therebetween within a plane orthogonal to the moving direction of the traverser, and are slidable on the inner walls of the feed-in preparation chamber or the feed-out preparation chamber.

The two plates, which are arranged in parallel with the mount sandwiched between them, can slide on the inner walls to prevent radioactive rays that enter from the imaging chamber both when the mount is communicating with the first opening and when it is communicating with the second opening. The shields sliding on the inner walls may not intend no gap between the shields and the inner walls. A small gap may be left between the inner walls and the shields to allow smooth movement of the shields.

In the inspection apparatus according to the above aspect of the present invention, a shortest distance from the first opening to the second opening may be longer than a distance between the first member and the second member.

This structure prevents the first opening and the second opening from communicating with each other, and prevents leakage of radioactive rays that enter from the imaging chamber in a reliable manner when the traverser is at any position.

The inspection apparatus according to the above aspect of the present invention may include a member that limits a movable range of the traverser to prevent the traverser positioned at one of the first opening and the second opening from moving in a direction away from the other one of the first opening and the second opening.

When the traverser is arranged between the first opening and the second opening, the shields prevent leakage of radioactive rays that enter from the imaging chamber. However, when the traverser moves outside this range, the first opening and the second opening can communicate with each other. To prevent this, a member that limits the movement of the traverser may be used.

The feed-in unit included in the feed-in preparation chamber may receive a subsequent inspection object into the feed-in preparation chamber before the imaging unit completes imaging. The traverser included in the feed-in preparation chamber may move the subsequent inspection object to the second opening before the imaging unit completes imaging.

In this manner, a subsequent inspection object is fed to a position immediately before the imaging chamber and waits while the imaging of the current inspection object is being performed. This shortens the time taken before starting the inspection, and improves the total inspection speed.

An inspection apparatus according to a second aspect of the present invention includes a feed-in preparation chamber, an imaging chamber, and a feed-out preparation chamber. Each of the feed-in preparation chamber and the feed-out preparation chamber includes a feed-in unit that receives an inspection object through a first opening, a traverser that translates the received inspection object to a second opening in a direction different from a direction in which the inspection object is received, and a feed-out unit that moves the inspection object in a direction different from the direction of the traverser, and discharges the inspection object through the second opening. The imaging chamber includes an imaging unit that images the inspection object received from the feed-in preparation chamber. The traverser includes a mount on which the inspection object is mountable, and a first shield and a second shield that move together with the mount. The first shield and the second shield are positioned to define a closed space together with opposing inner walls of the feed-in preparation chamber or the feed-out preparation chamber to allow the closed space to spatially separate the first opening from the second opening while the traverser is moving.

One or more aspects of the present invention are directed to an inspection apparatus including at least one of the above units. The above processes and units may be combined with one another unless any technical contradiction arises.

Advantageous Effects

The inspection apparatus that uses radioactive rays according to one or more embodiments of the present invention shortens the time for inspection and prevents leakage of radioactive rays.

BRIEF DESCRIPTION OF THE DRAWINGS

FIGS. 9A and 9B are diagrams describing a modification of the embodiment.

FIG. 10 is a diagram describing a modification of the embodiment.

DETAILED DESCRIPTION

An X-ray inspection apparatus according to one or more embodiments of the present invention performs non-destructive inspection of an object using image information obtained from X-ray imaging of the object. The embodiments are particularly directed to the structure for feeding an inspection object into and out of the X-ray inspection apparatus, and its control. In the embodiments described below, a substrate inspection apparatus reconstructs three-dimensional (3D) data representing components mounted on a substrate with oblique X-ray computed tomography (CT), and determines whether, for example, the solder is defective or non-defective based on the 3D data.

First Embodiment

Apparatus Overview

Figure 1:
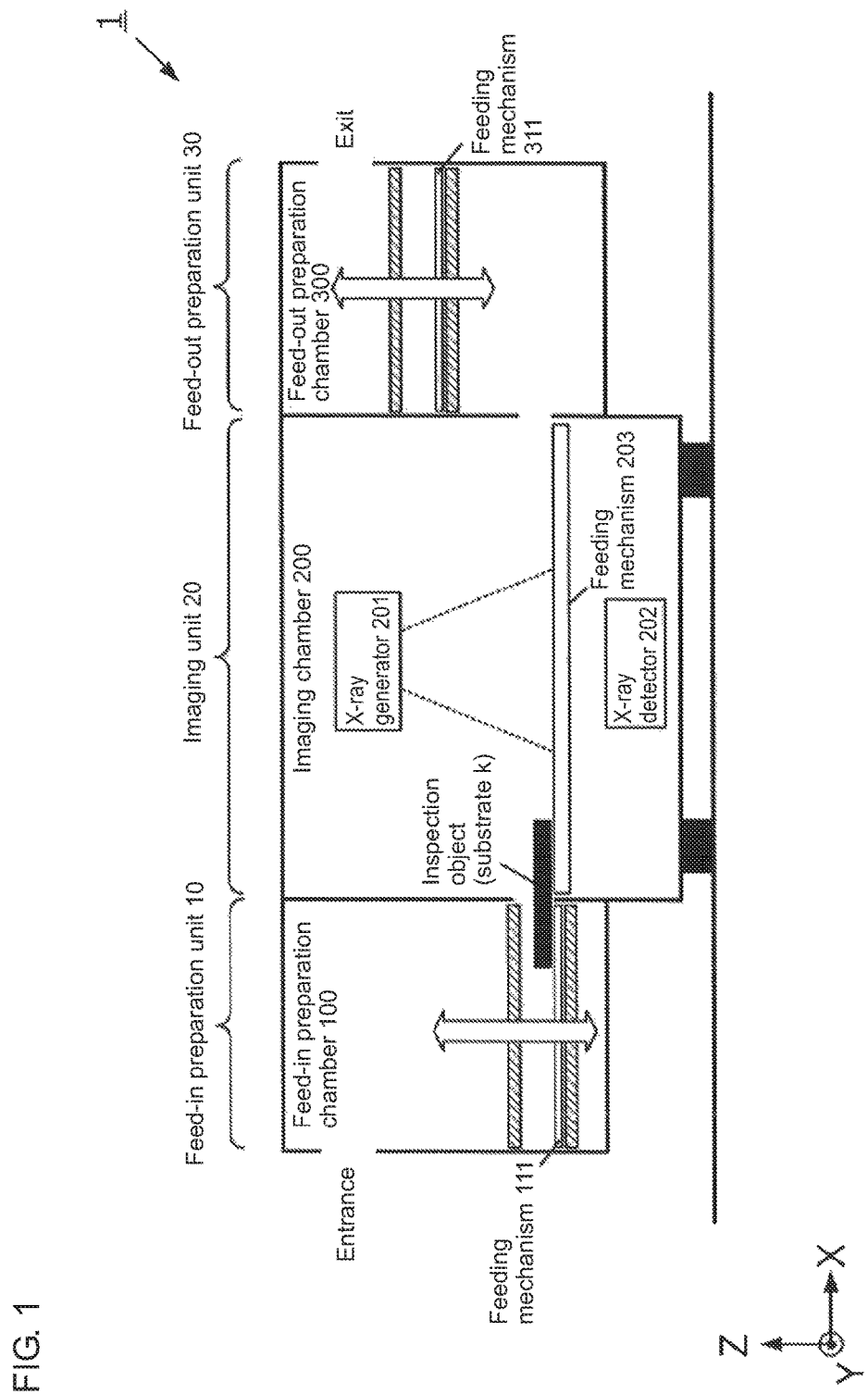
FIG. 1 is a schematic cross-sectional view of an X-ray inspection apparatus according to a first embodiment.
Figure 2:
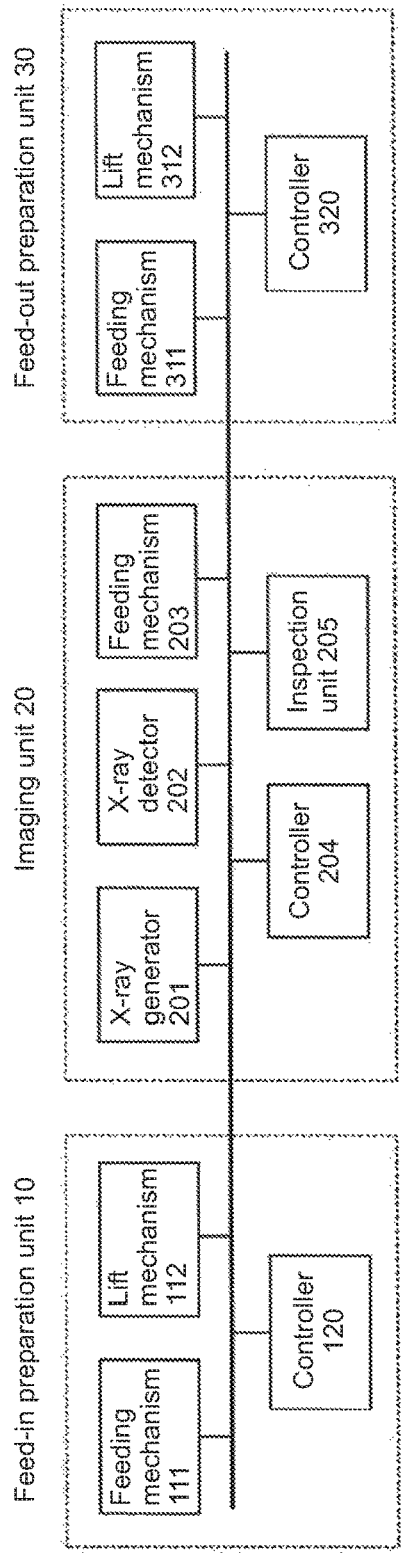
FIG. 2 is a block diagram showing the components and the functions of the X-ray inspection apparatus according to the first embodiment.

Referring to FIGS. 1 and 2, the structure of an X-ray inspection apparatus according to the present embodiment will now be described. FIG. 1 is a schematic cross-sectional view of an X-ray inspection apparatus 1 according to the present embodiment. FIG. 2 is a block diagram showing the components and the functions of the X-ray inspection apparatus 1. As shown in FIGS. 1 and 2, the X-ray inspection apparatus 1 includes a feed-in preparation unit 10, an imaging unit 20, and a feed-out preparation unit 30.

FIG. 1 is a diagram schematically showing a path on which a substrate is moved for inspection. A structure for preventing leakage of X-rays will be described later with reference to FIG. 3.

As shown in FIG. 1, the X-ray inspection apparatus 1 includes, in its body, the imaging unit 20 for imaging using X-rays. The feed-in preparation unit 10 for feeding a substrate K as an inspection object into the imaging unit 20 is arranged upstream (left in the figure) from the imaging unit 20. The feed-out preparation unit 30 for discharging the object is arranged downstream (right in the figure) from the imaging unit 20. The feed-in preparation unit 10 includes a feeding mechanism 111 for feeding the substrate received from an upstream process (e.g., a reflow process). The feeding mechanism 111 is movable upward and downward in the figure, and is connectable to a feeding mechanism 203, which is arranged in the imaging unit 20. The substrate K that is fed from the upstream process passes through the feed-in preparation unit 10 (feeding mechanism 111), and then is fed into the imaging unit 20 to undergo intended imaging and inspection. The substrate is then fed to a feeding mechanism 311, which is arranged in the feed-out preparation unit 30. The feeding mechanism 311 moves upward and downward in the figure, and feeds the substrate K through its exit to a downstream process. In this manner, the X-ray inspection apparatus 1 according to the present embodiment is installed on a production line (in-line) and is designed to automatically inspect substrates.

The feed-in preparation unit 10 will now be described.

The feed-in preparation unit 10 includes a box (hereafter, a feed-in preparation chamber 100) having an entrance through which the substrate K to be inspected is fed in, and an exit through which the substrate is fed to the imaging unit. The box is formed from a material that does not transmit X-rays.

The box through which the substrate to be inspected is moved is referred to as the feed-in preparation chamber 100, and the mechanisms arranged in the feed-in preparation chamber 100 and their controller are collectively referred to as the feed-in preparation unit 10. The feed-in preparation unit 10 includes the feed-in preparation chamber 100, the feeding mechanism 111, a lift mechanism 112, and a controller 120.

The feeding mechanism 111 moves an object mounted on it in the feeding direction (X-direction in the figure). Although the feeding mechanism 111 typically includes a linear actuator, a rail, and a belt conveyor, it may include other components. The substrate K fed from an upstream process is fed by the feeding mechanism 111 into the feed-in preparation chamber 100.

The feeding mechanism 111 is movable using the lift mechanism 112 in a direction orthogonal to the feeding direction of the substrate (Z-direction in the figure). The lift mechanism 112 may be driven by, for example, a linear actuator, or may be driven using power transferred with a belt or a chain to transfer the substrate to the feeding mechanism 111.

When the substrate K fed into the feed-in preparation chamber 100 reaches the exit, the feeding mechanism 111 feeds the substrate K into the imaging chamber 200, where the substrate K undergoes imaging and inspection.

The controller 120 controls the operations of the feeding mechanism 111 and the lift mechanism 112. The controller 120 may be implemented by, for example, software executed on a general-purpose computer, or using dedicated hardware. The control performed by the controller 120 will be described in detail later.

The imaging unit 20 will now be described.

The imaging unit 20 includes a box (hereafter, an imaging chamber 200) having an entrance through which the substrate K to be inspected is fed from the feed-in preparation chamber 100, and an exit through which the substrate is fed to a feed-out preparation chamber 300. The box is formed from a material that does not transmit X-rays.

The box, which defines a compartment for inspecting a substrate, is hereafter referred to as an imaging chamber 200. The components arranged in the imaging chamber 200 and their controller are collectively referred to as the imaging unit 20. The imaging unit 20 includes the imaging chamber 200, an X-ray generator 201, an X-ray detector 202, a feeding mechanism 203, a controller 204, and an inspection unit 205.

The X-ray generator 201 emits X-rays. The apparatus uses X-ray computerized tomography (CT) imaging, and thus uses an X-ray source that emits an X-ray cone beam, which diverges conically.

The X-ray detector 202 is a two-dimensional X-ray detector that detects X-rays that have been emitted from the X-ray source and have transmitted through the substrate under inspection. The X-ray detector 202 may be an image intensifier (I.I.) tube or a flat panel detector (FPD). Although the single X-ray detector is used in the present embodiment, a plurality of X-ray detectors may be used.

The X-ray generator 201 and the X-ray detector 202 are movable in two-dimensional directions using stages (not shown).

The feeding mechanism 203 is the same as the feeding mechanism 111, and will not be described.

The controller 204 controls X-ray imaging of the inspection object by controlling the operations of the X-ray generator 201, the X-ray detector 202, and the feeding mechanism 203.

In detail, the controller 204 controls reception of the substrate fed from the feed-in preparation chamber 100, discharge of the substrate that has undergone inspection, positioning of the X-ray generator 201 and the X-ray detector 202 using the stage (not shown), and X-ray emission performed by the X-ray generator 201.

The inspection unit 205 inspects the substrate using X-ray images detected by the X-ray detector 202. In the present embodiment, imaging is performed multiple times (several times to several tens of times) while changing the relative positions of the X-ray generator, the X-ray detector, and the inspection object to obtain X-ray transmission images captured from different angles. Based on the obtained data, three-dimensional data for the substrate is reconstructed. This imaging method is called oblique X-ray CT, and is suitable for inspecting a thin object, such as an electronic substrate. The computation method used for oblique X-ray CT is known, and will not be described.

The inspection unit 205 inspects the substrate based on the obtained three-dimensional data. The inspection unit 205 determines, for example, the positions of the components mounted on the substrate or the state of the solder (e.g., the solder wetting height or angle), and generates the results. The results may then be transmitted to a downstream process, or may be provided to the user of the apparatus through a display (not shown).

The controller 204 and the inspection unit 205 may each include a typical general-purpose arithmetic unit called a central processing unit (CPU). The controller 204 and the inspection unit 205 may also include a memory, such as a random-access memory (RAM), or a read-only memory (ROM), a hard disk drive (HDD), or a solid-state drive (SSD). The controller 204 and the inspection unit 205 may also include an input device with which a user can input instructions, such as a keyboard, a button, a switch, or a pointing device. The controller 204 and the inspection unit 205 may also include an output device that provides the inspection results to the user in the form of an image or a sound with, for example, a display or a speaker. In other words, these functional units may be implemented using a typical computer system.

Although the imaging unit 20 inspects the substrate using X-ray transmission images in the present embodiment, the imaging unit 20 may use a different mechanism for inspection. For example, the imaging unit 20 may further include a camera for capturing a visible light image, and may inspect the substrate using the visible light image.

The feed-out preparation unit 30 will now be described.

The feed-out preparation unit 30 includes a box (hereafter, the feed-out preparation chamber 300) having an entrance through which the substrate K that has undergone inspection is fed from the imaging chamber 200, and an exit through which the substrate is fed to a downstream process. The box is formed from a material that does not transmit X-rays.

The box through which the inspected substrate is moved is hereafter referred to as the feed-out preparation chamber 300, and the components arranged in the feed-out preparation chamber 300 and their controller are collectively referred to as the feed-out preparation unit 30. The feed-out preparation unit 30 includes the feed-out preparation chamber 300, a feeding mechanism 311, a lift mechanism 312, and a controller 320.

After the inspection, the substrate K is fed out of the imaging chamber 200, and is then moved to the feed-out preparation chamber 300 using the feeding mechanism 311. The feeding mechanism 311 and the lift mechanism 312 included in the feed-out preparation unit 30 are the same as the feeding mechanism 111 and the lift mechanism 112, and will not be described in detail.

The feed-out preparation chamber 300 also has an entrance and an exit in the same manner as the feed-in preparation chamber 100, and feeds the substrate K to a downstream process.

Structure for Preventing Leakage of X-rays

Figure 3:
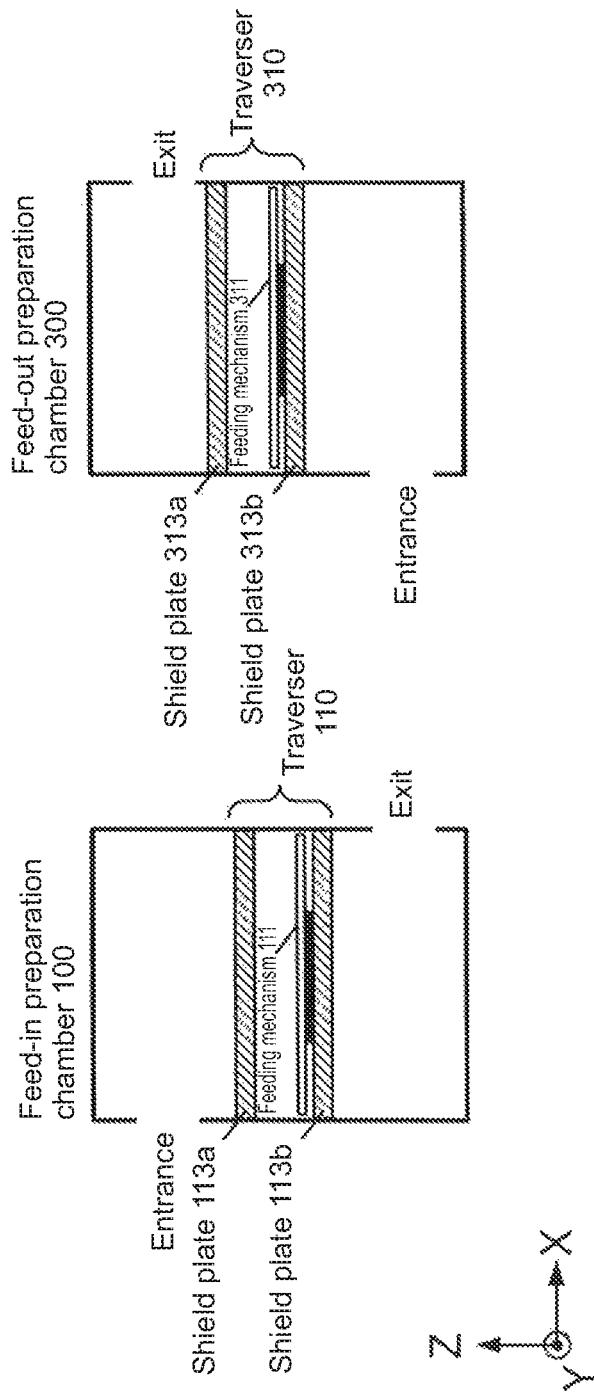
FIG. 3 is a cross-sectional view showing the structure of a feed-in preparation chamber 100 and a feed-out preparation chamber 300 in detail.

Referring now to FIG. 3, an X-ray shielding structure included in each of the feed-in preparation chamber 100 and the feed-out preparation chamber 300 for preventing leakage of X-rays outside will now be described. FIG. 3 is a cross-sectional view showing the structure of the feed-in preparation chamber 100 and the feed-out preparation chamber 300 in more detail.

Shield plates 113A and 113B are arranged in the XY plane to have the feeding mechanism 111 sandwiched between them. The shield plates 113A and 113B may be any typical members that prevent leakage of radioactive rays, and are typically formed from lead or tungsten.

The shield plates 113A and 113B have their four sides in contact with the inner walls of the feed-in preparation chamber 100 to prevent leakage of radioactive rays. The feeding mechanism 111, the shield plate 113A, and the shield plate 113B are movable together. In the present embodiment, these members are collectively referred to as a traverser 110.

The members included in the feed-out preparation chamber 300 are the same as the corresponding members described above except for the hundreds places in their reference numerals, and will not be described.

Figure 4:
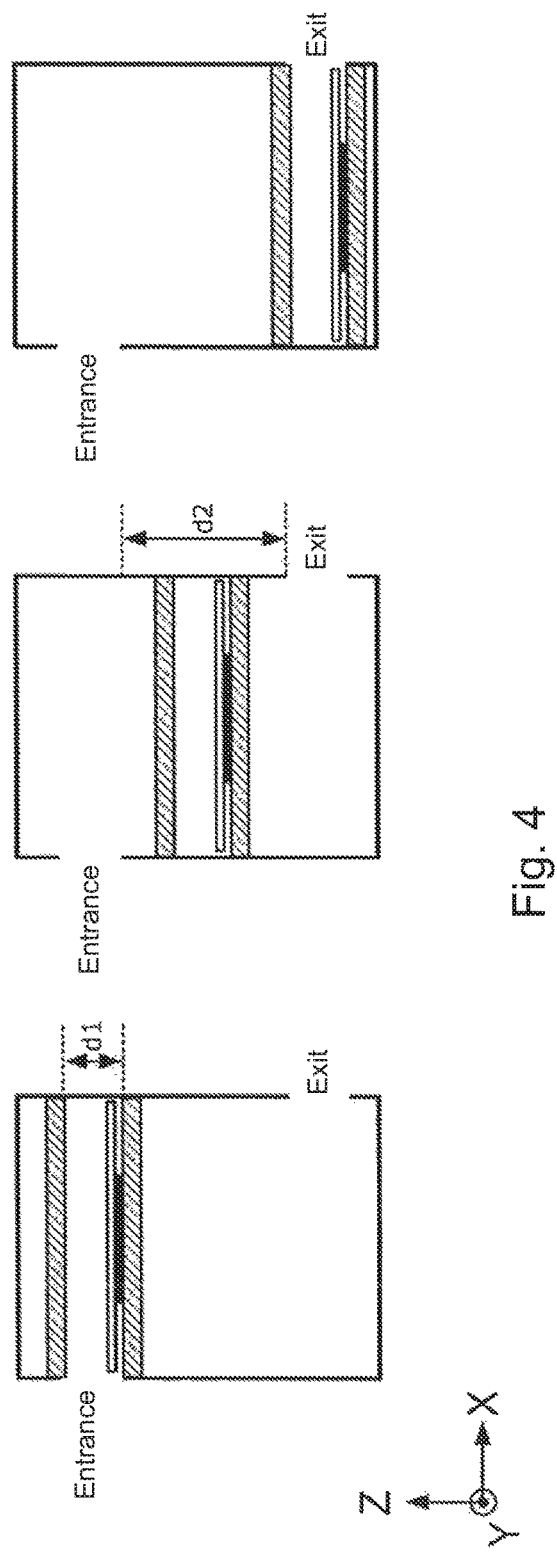
FIG. 4 is a diagram describing the movable range of a traverser 110.

FIG. 4 is a diagram describing the movable range of the traverser 110. As shown in FIG. 4, the movable range of the traverser 110 in Z-direction has its upper limit corresponding to the feeding mechanism 111 placed at the height of the entrance, and has its lower limit corresponding to the feeding mechanism 111 placed at the height of the exit. In other words, the shield plate 113A and/or the shield plate 113B is constantly located between the entrance and the exit. Although X-rays may enter the exit of the feed-in preparation chamber 100, which communicates with the imaging chamber 200, the entering X-rays are prevented by one or both of these shield plates from reaching the entrance of the feed-in preparation chamber 100. This structure spatially separates the imaging chamber 200 from outside the apparatus. The separation is maintained when the traverser 110 is at any position.

To enable this, the distance d1 between the shield plate 113A and the shield plate 113B is to be smaller than the shortest distance d2 between the entrance and the exit.

Although the feed-in preparation chamber 100 is described above, the substrate is fed from the imaging chamber 200 and discharged through the feed-out preparation chamber 300 in the same manner as in the feed-in preparation chamber 100.

Procedure

Figure 5:
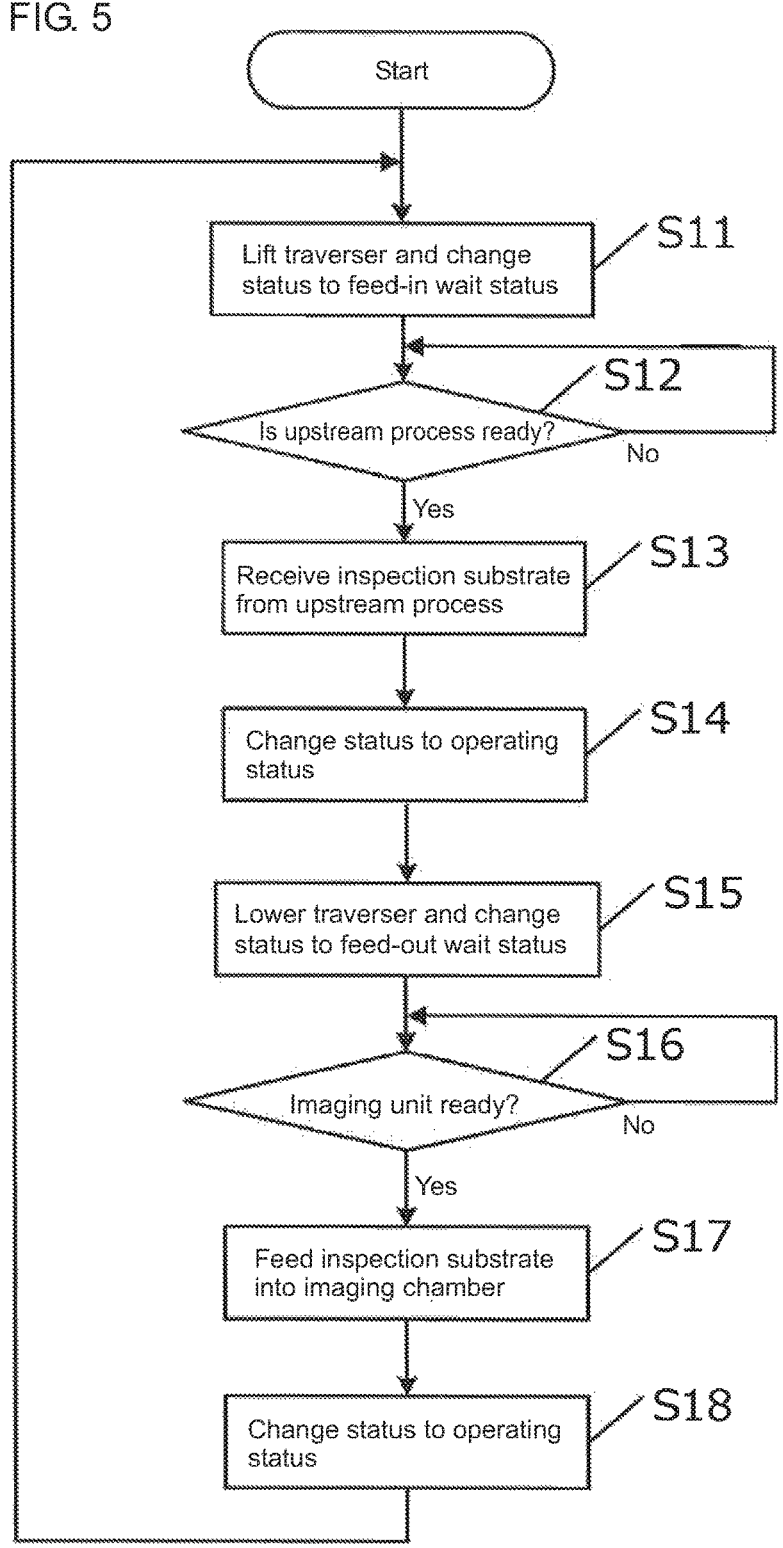
FIG. 5 is a flowchart showing a control procedure for feeding-in of a substrate.
Figure 6:
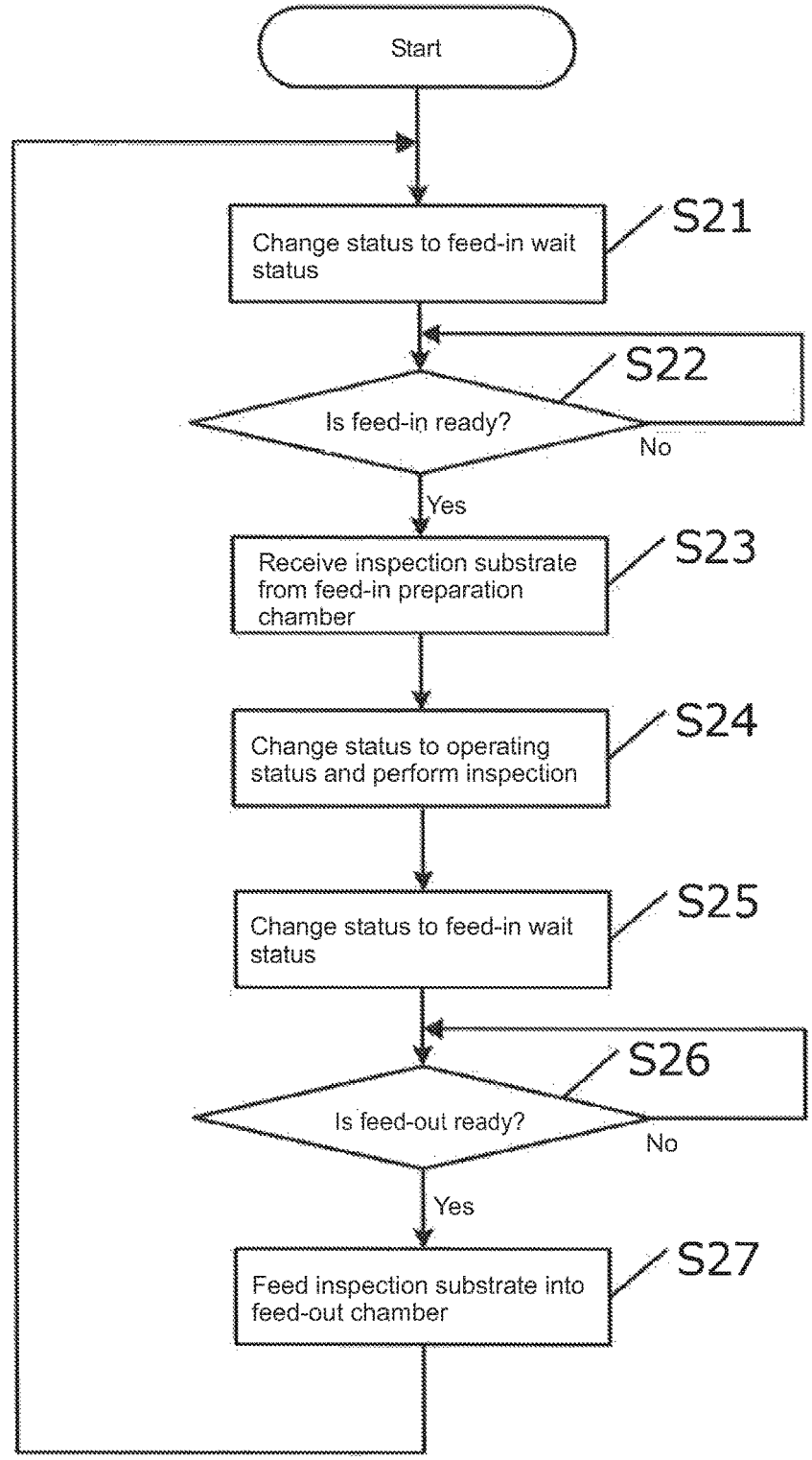
FIG. 6 is a flowchart showing a control procedure for inspection of a substrate.
Figure 7:
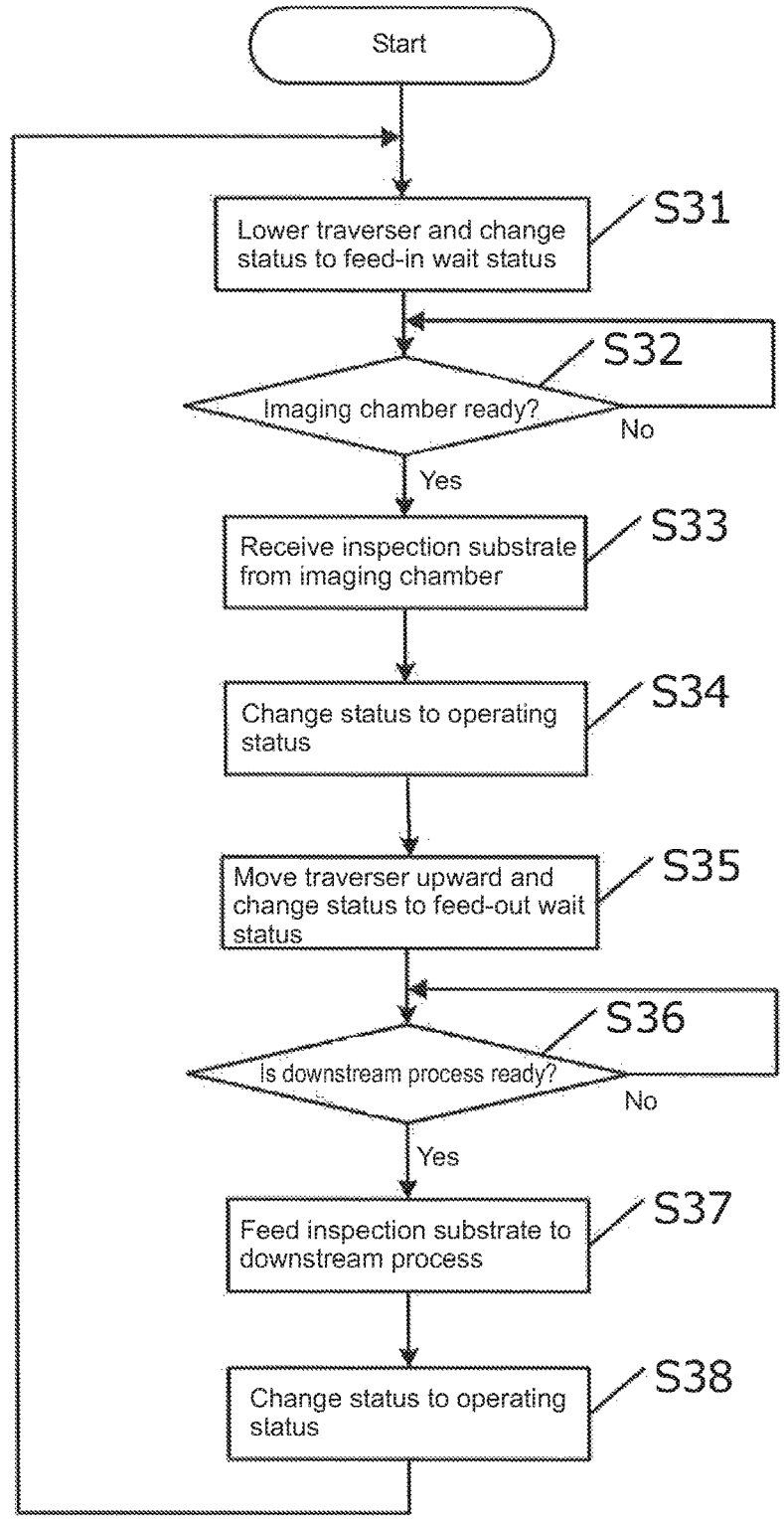
FIG. 7 is a flowchart showing a control procedure for feeding-out of a substrate.

Referring now to FIGS. 5 to 7, the control associated with feeding-in, inspection, and feeding-out of the substrate will be described.

FIG. 5 is a flowchart showing a control procedure for feeding-in of the substrate. The procedure shown in FIG. 5 is implemented by the controller 120 included in the feed-in preparation unit 10.

In this example, the feed-in preparation unit 10, the imaging unit 20, and the feed-out preparation unit 30 each hold its status, and determine whether to perform feeding in accordance with the status of those units. The status is one of three statuses, namely the feed-in wait status, the operating status, or the feed-out wait status.

In step S11, the traverser 110 is lifted using the lift mechanism 112, and then the status is changed to the feed-in wait status. This connects the feeding mechanism 111 to a feeding path in an upstream process.

In step S12, the controller determines whether the upstream process is ready. In this step, the controller determines whether an upstream device is ready for feeding the substrate to be inspected into the inspection apparatus. When the determination result is affirmative, the processing advances to step S13, and the feeding mechanism 111 is activated to receive the substrate to be inspected. When the result is negative, the controller waits for a predetermined wait time, and then repeats the determination.

When the substrate to be inspected is fed through the entrance, the status is changed to the operating status in step S14. In step S15, the traverser 110 is lowered, and the status is changed to the feed-out wait status. This connects the feeding mechanism 111 to the feeding mechanism 203.

In step S16, the controller determines whether the imaging chamber 200 is ready. In this step, the controller 120 determines whether the controller 204 included in the imaging unit 20 is ready for receiving the substrate. In this step, the determination result is affirmative when the status of the imaging unit 20 is the feed-in wait status, and is negative when the status is either the operating status or the feed-out wait status. When the determination result is affirmative, the processing advances to step S17, and the feeding mechanism 111 is activated to feed the substrate to be inspected into the imaging chamber. When the determination result is negative, the controller waits for a predetermined wait time, and then repeats the determination.

When the substrate to be inspected has been fed into the imaging chamber 200, the status is changed to the operating status in step S18. The processing then returns to step S11, and the traverser is moved to its initial position (lifted position).

FIG. 6 is a flowchart showing a control procedure for inspection of the substrate. The procedure shown in FIG. 6 is implemented by the controller 204 included in the imaging unit 20.

In step S21, the status is changed to the feed-in wait status.

In step S22, the controller determines whether the substrate is ready for being fed from the feed-in preparation chamber 100. In this step, the determination result is affirmative when the status of the feed-in preparation unit 10 is the feed-out wait status, and is negative when the status is either the operating status or the feed-in wait status. When the determination result is affirmative, the processing advances to step S23, and the feeding mechanism 203 is activated to receive the substrate to be inspected. When the determination result is negative, the controller waits for a predetermined wait time, and then repeats the determination.

When the substrate to be inspected is fed into the imaging chamber, the status is changed to the operating status in step S24. The substrate is inspected in step S24. More specifically, the substrate undergoes X-ray irradiation and imaging. The obtained images are transmitted to the inspection unit 205 to perform inspection. When the inspection is complete, the status is changed to the feed-out wait status in step S25.

In the above example, the processing advances to step S25 after the inspection is complete. In some embodiments, the imaging and the inspection may be performed in parallel. More specifically, the substrate may be discharged immediately when the inspection is started by the inspection unit 205 after the X-ray imaging is complete.

In step S26, the controller determines whether the feed-out preparation unit 30 is ready for receiving the substrate. In this step, the determination result is affirmative when the status of the feed-out preparation unit 30 is the feed-in wait status, and is negative when the status is either the operating status or the feed-out wait status. When the determination result is affirmative, the operation advances to step S27, and the feeding mechanism 203 is activated to discharge the substrate that has undergone inspection. When the determination result is negative, the controller waits for a predetermined wait time, and then repeats the determination.

FIG. 7 is a flowchart showing a control procedure for feeding-out of the substrate. The procedure shown in FIG. 7 is implemented by the controller 320 included in the feed-out preparation unit 30.

In step S31, the traverser 310 is lowered using the lift mechanism 312, and then the status is changed to the feed-in wait status. This connects the feeding mechanism 311 to the feeding mechanism 203.

In step S32, the controller determines whether the substrate is ready for being fed from the imaging chamber 200. In this step, the determination result is affirmative when the status of the imaging unit 20 is the feed-out wait status, and is negative when the status is either the operating status or the feed-in wait status. When the determination result is affirmative, the operation advances to step S33, and the feeding mechanism 311 is activated to receive the substrate that has been inspected. When the determination result is negative, the controller waits for a predetermined wait time, and then repeats the determination.

When the substrate that has been inspected is fed through the entrance, the status is changed to the operating status in step S34. In step S35, the traverser 310 is lifted, and the status is changed to the feed-out wait status.

In step S36, the controller determines whether the downstream process is ready. In this step, the controller determines whether a device installed in the downstream process is ready for feeding the substrate from the inspection apparatus. When the determination result is affirmative, the processing advances to step S37, and the feeding mechanism 311 is activated to discharge the substrate that has undergone inspection. When the determination is negative, the controller waits for a predetermined wait time, and then repeats the determination.

When the substrate has been discharged, the status is changed to the operating status in step S38. The processing advances to step S31, and the traverser is moved to its initial position (lowered position).

As described above, the inspection apparatus according to the present embodiment prevents leakage of X-rays generated in the imaging chamber using the shields included in the traverser. This structure eliminates a mechanism that opens and closes the X-ray shields independently, and thus reduces the cost of the apparatus. This structure also enables the feed-in and feed-out operations to be performed during X-ray irradiation in the imaging chamber, and thus readily shortens the time taken for the inspection. Additionally, the feed-in preparation unit and the feed-out preparation unit operate independently of each other. This allows a subsequent substrate to be fed into the inspection chamber before the currently inspected substrate is completely discharged from the inspection apparatus. This shortens the interval of X-ray imaging operations, and thus shortens the total inspection time.

Second Embodiment

Figure 8:
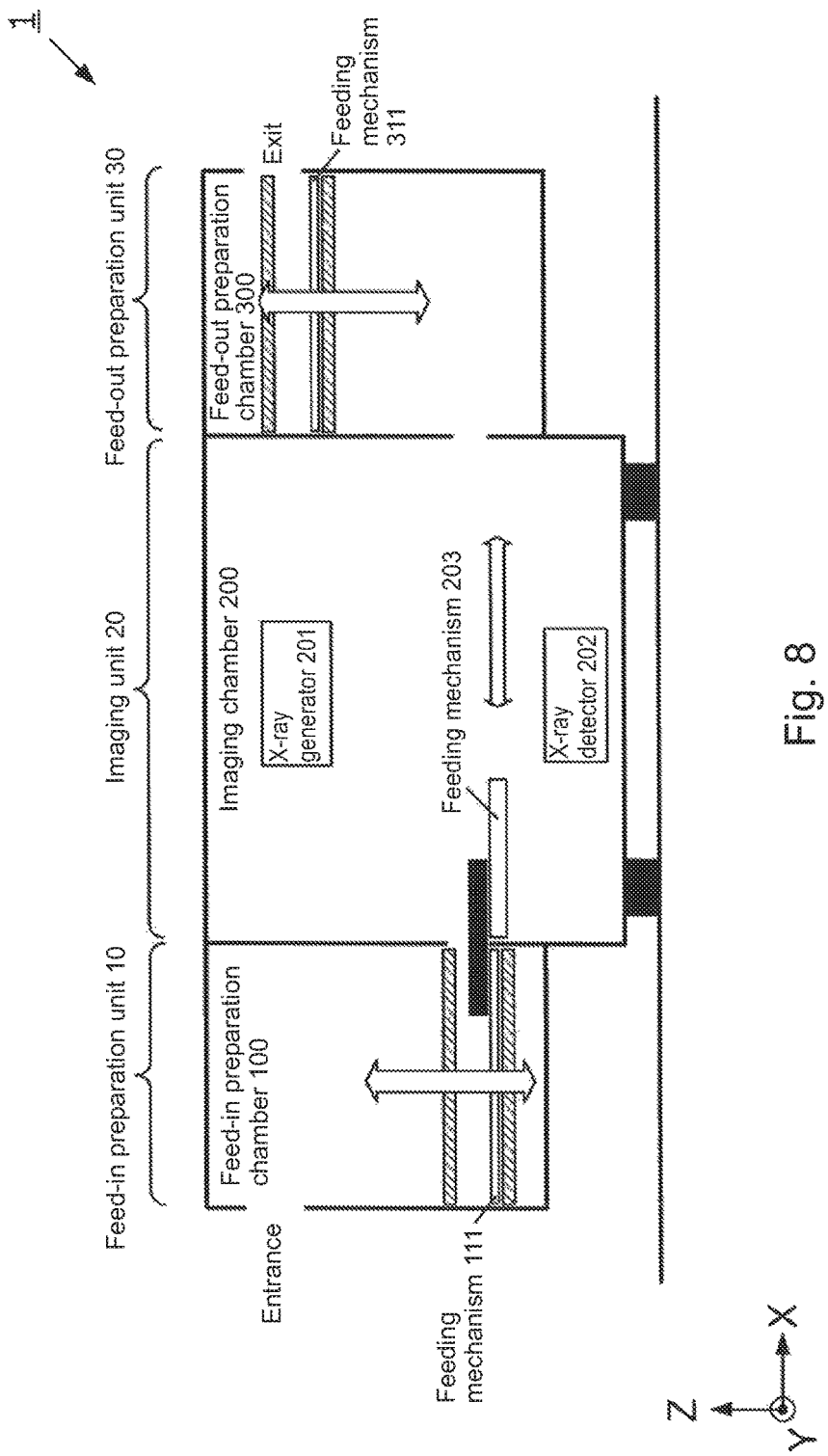
FIG. 8 is a diagram describing a modification of the embodiment.

The feeding mechanism 203 in the first embodiment extends across the imaging chamber 200 to allow a mounted substrate to be moved on the feeding mechanism 203. In the second embodiment, a feeding mechanism 203 is moved to move a substrate together. FIG. 8 is a schematic cross-sectional view of an X-ray inspection apparatus 1 according to the second embodiment.

As shown in the figure, the feeding mechanism 203 in the present embodiment is movable in X-direction in the figure.

In the second embodiment, the feeding mechanism 203 is moved to a position at which it can receive a substrate before the processing in step S21 is started. The feeding mechanism 203 is also moved to a position at which it can discharge the substrate before the processing in step S25 is started. After the completion of the processing in step S27, the status is temporarily changed to the operating status until the feeding mechanism 203 is moved to a position at which it can receive the substrate. This is another embodiment of the present invention.

Modifications

The embodiments disclosed herein should not be construed to be restrictive, but may be modified within the spirit and scope of the claimed invention. The technical features disclosed in different embodiments may be combined in other embodiments within the technical scope of the invention.

For example, although the above embodiments are directed to the apparatuses for inspecting substrates, the present invention is applicable to X-ray non-destructive inspection for various other inspection objects, in addition to substrates. The present invention is also applicable to any other imaging method, in addition to the imaging method using oblique X-ray CT. Although the structure according to the embodiments of the present invention is suitable for an imaging method that uses a cone beam for effective shielding, it is also applicable to other imaging methods using a fan beam or a highly directional beam.

Further, although the apparatuses according to the above embodiments have a single inspection line in the imaging chamber, the apparatuses may have two or more lines in the imaging chamber. For example, the apparatuses may include a plurality of inspection lines when a longer time is taken for X-ray imaging than for an operation in an upstream (downstream) process. In this case, the imaging chamber may have a plurality of entrances and a plurality of exits. For example, when the entrances (exits) are arranged in Z-direction, the traverser may be controlled to stop at an intended entrance (exit). When the entrances (exits) are arranged in Y-direction, the traverser may include an additional mechanism that shifts the substrate in Y-direction. The traverser may further include a plurality of feeding mechanisms arranged in parallel. The number of inspection lines may be determined to balance between the processing amount and the processing time.

Further, although the inspection object is fed in X-direction and the traverser is moved in Z-direction in the above embodiments, the embodiments are not limited to this structure. For example, the traverser may be movable in the depth direction in the figure (Y-direction). This modification is suitable for inspecting a substrate that is thick in the vertical direction (Z-direction) and thin in the horizontal direction (Y-direction). In this case, a plurality of shield plates may be arranged in parallel in the depth direction in the figure. The direction in which the traverser moves and the positions at which the shield plates are arranged may be changed as appropriate for the design.

Further, members may be added to prevent the traverser from moving outside its movable range. For example, as shown in FIG. 9A, movement of the traverser into an unintended area due to mispositioning may allow communication between the entrance and the exit, and may cause X-ray leakage. Cushions may be arranged as shown in FIG. 9B to limit the movable range of the traverser. This prevents the traverser from moving outside the intended movable range, and improves safety.

Although the traverser in the above embodiments includes the whole plates that slide on the inner walls of the feed-in preparation chamber (feed-out preparation chamber) as the shield plates, the shield plates may not be whole plates, and also may not slide on the inner walls. For example, as shown in FIG. 10, a small gap may be left between the shield plates and the inner walls. The size of the gap may be determined in accordance with the permissible amount of X-ray leakage. In particular, shield plates with side walls shown in FIG. 10 are appropriate and can also serve as the cushions in FIGS. 9A and 9B.

REFERENCE SIGNS LIST 10 feed-in preparation unit
20 imaging unit
30 feed-out preparation unit
100 feed-in preparation chamber
111 feeding mechanism
112 lift mechanism
120 controller
200 imaging chamber
201 X-ray generator
202 X-ray detector
203 feeding mechanism
204 controller
205 inspection unit
300 feed-out preparation chamber
311 feeding mechanism
312 lift mechanism
320 controller

The invention claimed is:

1. An inspection apparatus, comprising:
a feed-in preparation chamber;
an imaging chamber; and
a feed-out preparation chamber, wherein
each of the feed-in preparation chamber and the feed-out preparation chamber comprises:
  a feed-in conveyor configured to receive an inspection object through a first opening,
  a traverser configured to translate the received inspection object to a second opening in a direction different from a direction in which the inspection object is received, and
  a feed-out conveyor configured to move the inspection object in a direction different from a moving direction of the traverser, and discharge the inspection object through the second opening, and
the imaging chamber comprises:
  an imaging unit that images the inspection object that is received from the feed-in preparation chamber, wherein the traverser comprises:
    a mount on which the inspection object is mountable, and
    a shield in contact with each opposing inner wall of the feed-in preparation chamber or the feed-out preparation chamber, the shield configured to move together with the mount, and prevent radioactive rays that enter through one of the first opening and the second opening and propagate in the moving direction of the traverser from reaching the other one of the first opening and the second opening.

2. The inspection apparatus according to claim 1, wherein the shield comprises a first member and a second member, and the first member and the second member are positioned to define a closed space together with the opposing inner walls of the feed-in preparation chamber or the feed-out preparation chamber while the traverser is moving.

3. The inspection apparatus according to claim 2, wherein the first opening and the second opening are spatially separated by the closed space.

4. The inspection apparatus according to claim 2, wherein the first member and the second member comprise plates that are arranged in parallel with the mount sandwiched therebetween within a plane orthogonal to the moving direction of the traverser, and are slidable on the opposing inner walls of the feed-in preparation chamber or the feed-out preparation chamber.

5. The inspection apparatus according to claim 4, wherein a shortest distance from the first opening to the second opening is longer than a distance between the first member and the second member.

6. The inspection apparatus according to claim 1, further comprising:

a member configured to limit a movable range of the traverser to prevent the traverser positioned at one of the first opening and the second opening from moving in a direction away from the other one of the first opening and the second opening.

7. The inspection apparatus according to claim 1, wherein the feed-in conveyor comprised in the feed-in preparation chamber is configured to feed a subsequent inspection object into the feed-in preparation chamber before the imaging unit completes imaging.

8. The inspection apparatus according to claim 7, wherein the traverser comprised in the feed-in preparation chamber is configured to move the subsequent inspection object to the second opening before the imaging unit completes imaging.

9. An inspection apparatus, comprising:
a feed-in preparation chamber;
an imaging chamber; and
a feed-out preparation chamber, wherein
each of the feed-in preparation chamber and the feed-out preparation chamber comprises:

a feed-in conveyor configured to receive an inspection object through a first opening, a traverser configured to translate the received inspection object to a second opening in a direction different from a direction in which the inspection object is received, and a feed-out conveyor configured to move the inspection object in a direction different from a moving direction of the traverser, and discharge the inspection object through the second opening, and the imaging chamber comprises an imaging unit imaging the inspection object that is received from the feed-in preparation chamber, wherein the traverser comprises:

a mount on which the inspection object is mountable, and a first shield and a second shield each in contact with each opposing inner wall of the feed-in preparation chamber or the feed-out preparation chamber and configured to move together with the mount, and the first shield and the second shield are positioned to define a closed space together with the opposing inner walls of the feed-in preparation chamber or the feed-out preparation chamber to allow the closed space to spatially separate the first opening from the second opening while the traverser is moving.

10. The inspection apparatus according to claim 3, wherein the first member and the second member comprise plates that are arranged in parallel with the mount sandwiched therebetween within a plane orthogonal to the moving direction of the traverser, and are slidable on the inner walls of the feed-in preparation chamber or the feed-out preparation chamber.

11. The inspection apparatus according to claim 10, wherein a shortest distance from the first opening to the second opening is longer than a distance between the first member and the second member.

* * * * *